United States Patent [19] [11] 4,212,861
Theobald et al. [45] Jul. 15, 1980

[54] ISOXAZOLE-5-ALKYL DITHIOPHOSPHORIC ACID DERIVATIVES

[75] Inventors: Hans Theobald, Limburgerhof; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 888,297

[22] Filed: Mar. 20, 1978

Related U.S. Application Data

[63] Continuation-in-part of Ser. No. 732,205, Oct. 14, 1976, abandoned.

[30] Foreign Application Priority Data

Nov. 7, 1975 [DE] Fed. Rep. of Germany ....... 2549961

[51] Int. Cl.$^2$ ...................... C07D 261/10; A01N 9/36
[52] U.S. Cl. .................................... 424/200; 548/119
[58] Field of Search .................. 260/307 H; 424/200; 548/119 (U.S. only)

[56] References Cited

U.S. PATENT DOCUMENTS

| | | | |
|---|---|---|---|
| 3,562,288 | 2/1971 | Scherer et al. | 260/307 |
| 3,794,724 | 2/1974 | O'Melia | 424/200 |
| 3,867,396 | 2/1975 | Dawes et al. | 260/308 R |
| 3,867,397 | 2/1975 | Bohner et al. | 260/308 R |
| 3,886,274 | 5/1975 | Kristinsson et al. | 424/200 |
| 3,888,874 | 6/1975 | Dawes et al. | 260/308 R |

FOREIGN PATENT DOCUMENTS

| | | | |
|---|---|---|---|
| 848023 | 5/1977 | Belgium | 260/307 H |
| 766383 | 10/1976 | South Africa | 260/307 H |
| 453060 | 10/1978 | Spain | 260/307 H |
| 1261158 | 1/1972 | United Kingdom. | |

*Primary Examiner*—Anton H. Sutto
*Attorney, Agent, or Firm*—Keil & Witherspoon

[57] ABSTRACT

Dithiophosphoric acid derivatives bearing, as ester component, an isoxazole-5-alkyl radical substituted in the 3-position by alkyl of 1 to 6 carbon atoms, a process for their manufacture by reaction of isoxazole-5-alkyl halides substituted in the 3-position by alkyl with salts of dithiophosphoric acid derivatives, and pesticides containing these isoxazole-5-alkyl dithiophosphoric acid derivatives as active ingredients. The active ingredients according to the invention may be used for combatting pests such as sucking and biting insects, especially Lepidoptera, Diptera and mites.

12 Claims, No Drawings

ISOXAZOLE-5-ALKYL DITHIOPHOSPHORIC ACID DERIVATIVES

This application is a continuation-in-part of U.S. patent application Serial No. 732,205, filed October 14, 1976, and now abandoned.

The present invention relates to new phosphoric acid derivatives, a process for their manufacture, and pesticides containing these phosphoric acid derivatives as active ingredient.

The phosphoric acid derivatives of the invention are esters and have the formula

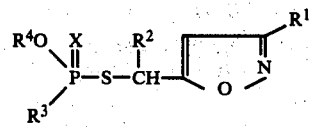

where X denotes oxygen or sulfur, $R^1$ and $R^4$ denote identical or different, linear or branched alkyl groups of a maximum of 6 carbon atoms, $R^2$ denotes hydrogen or alkyl or a maximum of 3 carbon atoms, and $R^3$ denotes linear or branched alkylthio of a maximum of 6 carbon atoms.

Examples of linear or branched alkyl groups for $R^1$ and $R^4$ in formula I are methyl, ethyl, propyl, isopropyl, butyl, pentyl and hexyl; alkyl groups for $R^2$ are methyl, ethyl, propyl and isopropyl; examples of thio substituents for $R^3$ are methylthio, ethylthio, n-propylthio, isopropylthio, butylthio, and hexylthio.

Preferred substituents for $R^1$ and $R^4$ are methyl, ethyl, propyl and isopropyl; preferred for $R^2$ are hydrogen and methyl; preferred for $R^3$ are methylthio, ethylthio, n-propylthio, isopropylthio, n-butylthio, isobutylthio, sec-butylthio and t-butylthio.

The new phosphoric acid derivatives are obtained by reacting salts of phosphoric acid derivatives of the formula II with isoxazole derivatives of the formula III to give the phosphoric acid derivatives of the invention of the formula I:

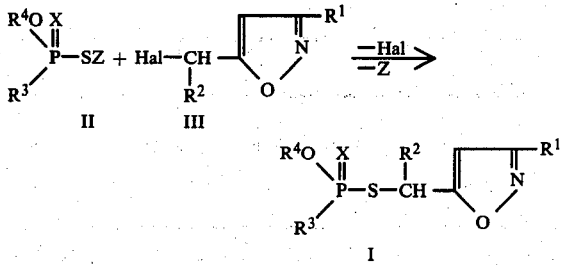

$R^1$, $R^2$, $R^3$, $R^4$ and X have the above meanings, Hal denotes halogen and Z denotes an alkali metal ion, an equivalent amount of an alkaline earth metal ion, or an ammonium ion optionally substituted by alkyl.

As halogen, there may be used fluorine, chlorine, bromine and iodine; it is, however, preferred to use chlorine and bromine. As alkali metal ions it is preferred to use sodium and potassium, as alkaline earth metal ions magnesium and calcium, and as ammonium ion the unsubstituted ion and methyl-, ethyl-, propyl-, isopropyl-, dimethyl-, diethyl-, trimethyl-, triethyl-, tetramethyl- and tetraethylammonium.

The process according to the invention is generally carried out in the presence of diluents. Examples of such diluents are water, lower alcohols such as methanol, ethanol and propanol, nitriles such as acetonitrile, ketones such as acetone and methyl ethyl ketone, ethers such as dioxane and tetrahydrofuran, and aromatic compounds such as benzene, toluene, xylenes, chlorobenzenes, dimethylformamide and dimethyl sulfoxide. Both reactants may be reacted in an equimolar ratio or either in excess. Reaction temperatures are from 0° to 150° C., preferably from 20° to 100° C.

The phosphoric acid salts of the formula II may be prepared by known methods (Houben-Weyl, Methoden der organischen Chemie, 12/2, pp. 131 et seq., Georg Thieme-Verlag, Stuttgart, 1964; German Laid-Open Application DOS No. 2 506 618.6).

The isoxazole derivatives of the formula III used as starting compounds may be obtained by 1,3-dipolar cycloaddition of nitrile oxides of the formula IV to acetylene compounds of the formula V in accordance with the following equation:

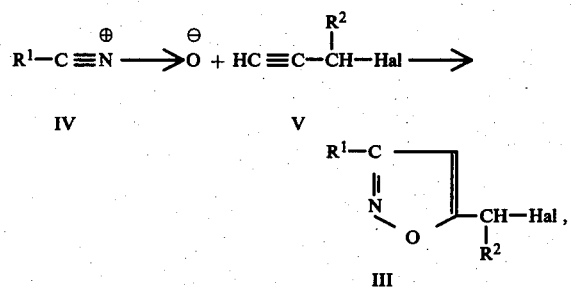

where $R^1$, $R^2$ and Hal have the above meanings.

The nitrile oxides of the formula IV required as starting compounds may be easily prepared by generally known processes (Houben-Weyl, Methoden der organischen Chemie, 10/3, p. 837, Georg Thieme-Verlag, Stuttgart, 4th ed., 1965; J. Org. Chem., 28, 1150, 1963), for instance by reaction of aliphatic nitro compounds of the formula VI with water-eliminating agents or by dehydrohalogenation of hydroxamic halides, especially chlorides, of the formula VII.

Aliphatic nitro compounds may be prepared by the processes described in Houben-Weyl, Methoden der organischen Chemie, 10/1, pp. 1–461, Georg Thieme-Verlag, Stuttgart, 4th ed., 1971, and hydroxamic halides by the processes described in Houben-Weyl, Methoden der organischen Chemie, 10/4, pp. 98–128, George Thieme-Verlag, Stuttgart, 4th ed.

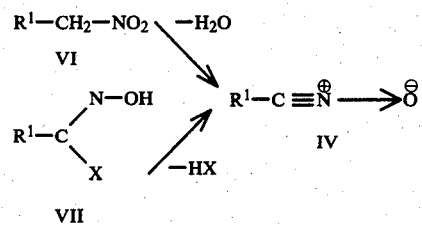

The nitrile oxides of the formula IV and the acetylene compounds of the formula V may be reacted in equimolar amounts; alternatively, either of the two reactants may be used in excess.

It is, however, not necessary to isolate the nitrile oxides of the formula IV before the reaction of the invention; indeed it is advantageous to produce the nitrile oxides of the formula IV in the presence of the acetylene compounds of the formula V. The reactive nitrile oxides then react in situ with the acetylene compounds to give isoxazoles of the formula III.

A suitable solvent in which the reaction proceeds is an excess of the acetylene compound of the formula V. Examples of other suitable solvents are aromatic compounds, such as benzene, toluene, xylene and halogenated aromatic compounds; ketones, such as acetone, methyl ethyl ketone and diisopropyl ketone; ethers, such as dioxane, diethyl ether and tetrahydrofuran; and chlorinated hydrocarbons, such as dichloroethane, chloroform and methylene chloride.

It is advantageous to carry out the reaction at atmospheric pressure and temperatures of from −20° to +150° C.; temperatures of from 0° to 100° C. are preferred.

To intercept hydrogen halide formed in the reaction it is expedient to add a base, e.g., a tertiary amine.

The following examples illustrate the process for the manufacture of isoxazole derivatives of the formula III. The structure is established with the aid of $^1$H-NMR spectroscopy and $^{13}$C-NMR spectroscopy.

Parts by weight bear the same relation to parts by volume as kilograms to liters.

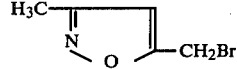
A.

238 parts by weight of propargyl bromide, 476 parts by weight of phenyl isocyanate and 158 parts by weight of nitroethane are dissolved in 1,500 parts by volume of toluene; at 15° to 20° C., 1 part by volume of triethylamine is then added to activate the phenyl isocyanate. The temperature is kept for 3 hours at 15° to 30° C., 1 part by volume of triethylamine being added per hour. Subsequently, the mixture is stirred for 1 hour at 70° C., and then cooled. The precipitate is suction filtered and the residue washed with 1,000 parts by volume of toluene. The combined filtrates are concentrated and the residue is distilled under an oil pump vacuum. At 59° to 61° C./0.2 mm Hg, 310 parts by weight (88% of theory) of 5-bromomethyl-3-methylisoxazole ($n_D^{25}$: 1.5168) distil over.

| $C_5H_6BrNO$ (176) | C | H | N | Br |
|---|---|---|---|---|
| Calc.: | 34.2 | 3.4 | 7.9 | 45.5 |
| Found: | 34.0 | 3.4 | 8.0 | 45.4 |

60 MHz nmr spectrum (CDCl$_3$; δ values): 2.3 (3H, s) 4.44 (2H, s) 6.15 (1H, s).

$^{13}$C-nmr spectrum (CDCl$_3$; ppm values relative to TMS): 167.2 (C), 160.1 (C), 104.5 (CH), 18.8 (CH$_2$), 11.3 (CH$_3$).

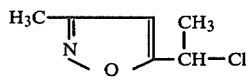
B.

93.5 parts by weight of acetohydroximoyl chloride (Ber. dtsch. chem. Ges., 40, 1677, 1907) and 90 parts by weight of isobutynyl chloride are stirred into 1,500 ml of benzene; at 15° to 20° C., 105 parts by weight of triethylamine is then added dropwise. The mixture is then stirred for 1 hour at 20° to 25° C. and for 1 hour at 70° C. After cooling, the mixture is filtered and the filtrate concentrated. The distillate which remains is distilled under an oil pump vacuum. There is obtained 133 parts by weight (92% of theory) of 5-(1-chloroethyl)-3-methyl isoxazole having a boiling point of 48° to 50° C./0.05 mm Hg; $n_D^{25}$: 1.4740.

| $C_6H_8NOCl$ (145.5) | C | H | N | Cl |
|---|---|---|---|---|
| Calc.: | 49.6 | 5.5 | 9.7 | 24.5 |
| Found: | 49.5 | 5.7 | 10.0 | 24.0 |

60 MHz nmr spectrum (CDCl$_3$; δ values): 1.78 (d, 3H); 2.3 (s, 3H); 5.05 (9, 1H); 6.09 (s, 1H).

$^{13}$C nmr spectrum (CDCl$_3$; ppm values relative to TMS): 171.5 (C); 159.8 (C); 102.5 (CH); 47.4 (CH); 23.3 (CH$_3$); 11.5 (CH$_3$).

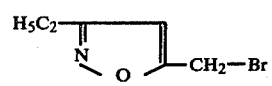
C.

119 parts by weight of propargyl bromide, 95 parts by weight of nitropropane and 440 parts by weight of triethylamine are dissolved in 1,200 parts by volume of chloroform; at 0° C., 155 parts by weight of phosphoroxy chloride is then added dropwise. The mixture is then heated for 30 minutes at 20° C. and then refluxed for 2 hours. After cooling, the mixture is filtered and concentrated, and the residue is taken up in water. The water phase is extracted again with toluene, and the combined toluene phases are washed with water and then dried over sodium sulfate. The sodium sulfate is then separated and the filtrate concentrated; the residue is distilled under an oil pump vacuum. At 78° C. to 79° C./0.1 mm Hg, 150 parts by weight (79% of theory) of 5-bromomethyl-3-ethyl isoxazole distil over; $n_D^{25}$: 1.5108.

| $C_6H_8BrNO$ (190) | C | H | N | Br |
|---|---|---|---|---|
| Calc.: | 37.9 | 4.2 | 7.4 | 42.0 |
| Found: | 38.0 | 4.6 | 7.6 | 41.7 |

The following compounds are obtained analogously:

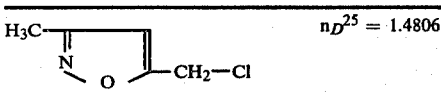 $n_D^{25} = 1.4806$

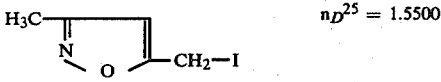 $n_D^{25} = 1.5500$

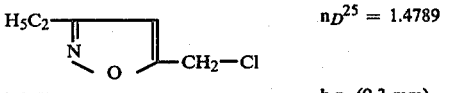 $n_D^{25} = 1.4789$

 b.p. (0.3 mm) = 75°–77° C.

The following examples illustrate the preparation of the new phosphoric acid derivatives.

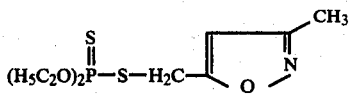

1.

17 parts by weight of 3-methyl-5-bromomethyl isoxazole and 21 parts by weight of O,O-diethyldithiophosphoric acid ammonium are stirred in 80 parts by volume of acetonitrile for 5 hours at 50° C. After the mixture has been cooled, the precipitate is filtered off. The acetonitrile is removed and the residue taken up in toluene. The toluene phase is washed with 5% aqueous sodium carbonate solution and with water, and then dried over $Na_2SO_4$. After filtration, the toluene is distilled off and the residue is subjected to incipient distillation at 60° C./1 mm Hg. There is obtained 26 parts by weight of a yellowish oil; yield: 96% of theory.

| $C_9H_{16}NPO_3S_2$ (281) | C | H | N | P | S |
|---|---|---|---|---|---|
| Calc.: | 38.4 | 4.2 | 5.0 | 11.0 | 22.8 |
| Found: | 38.2 | 4.0 | 5.4 | 10.8 | 22.7 |

100 MHz nmr spectrum ($CDCl_3$, δ values): 1.3 (6H), 2.22 (3H), 3.9–4.3 (6H), 4.1 (1H).

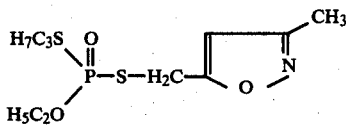

2.

158 parts by weight of 3-methyl-5-bromomethyl isoxazole an 245 parts by weight of O-ethyl-S-n-propyldithiophosphoric acid dimethylammonium are stirred in 800 parts by volume of water and 10 parts of volume of dimethylformamide for 6 hours at 50° to 60° C. The mixture is then cooled and the precipitated oil is separated and taken up in ether. The ether phase is washed with water and dried with $Na_2SO_4$. After filtration, the ether is withdrawn and the residue subjected to incipient distillation at 60° C./0.1 mm Hg. There is obtained 245 parts by weight of a pale yellow oil; yield: 92% of theory.

| $C_{10}H_{18}NPO_5S_2$ (295) | C | H | N | S | P |
|---|---|---|---|---|---|
| Calc.: | 40.7 | 6.1 | 4.7 | 21.7 | 10.5 |
| Found: | 41.0 | 6.0 | 5.2 | 21.2 | 10.2 |

60 MHz nmr spectrum ($CDCl_3$, δ values): 0.85 (3H), 1.18 (3H), 1.54 (2H), 21.5 (3H), 2.66 (2H), 3.8–4.2 (4H), 6.03 (1H).

The following compounds are obtained analogously:

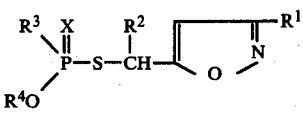

| No. | $R^1$ | $R^2$ | $R^3$ | $R^4$ | X | MHz nmr spectrum δ-values (LM) |
|---|---|---|---|---|---|---|
| 3 | $C_2H_5$ | H | $OC_2H_5$ | $C_2H_5$ | S | ($CDCl_3$, 60 MHz); 1.1–1.5 (9H), 2.7 (2H), 4.13 (2H), 3.8–4.4 (4H), 6.17 (1H). |
| 4 | $CH_3$ | H | cyclohexyl | $C_2H_5$ | O | ($CDCl_3$, 60 MHz); 1.38 (3H), 2.18 (3H), 3.62–4.5 (4H), 5.9 (1H), 7.4–8.1 (5H). |
| 5 | $CH_3$ | H | $S$-$i$-$C_3H_7$ | $C_2H_5$ | O | ($CDCl_3$, 220 MHz); 1.3 (3H), 1.33–1.44 (6H), 2.13 (3H), 3.23 (1H), 3.72–3.91 (4H), 5.58 (1H). |
| 6 | $CH_3$ | $CH_3$ | cyclohexyl | $C_2H_5$ | O | ($CDCl_3$, 60 MHz; 1.44 (3H), 2.25 (3H), 4.0–4.85 (3), 5.95 (1H), 7.2–8.05 (5H). |
| 7 | $CH_3$ | H | $S$-$n$-$C_3H_7$ | $n$-$C_3H_7$ | O | ($CDCl_3$, 60 MHz); 0.8–1.17 (6H) 1.42–2.0 (4H), 2.3 (3H), 2.75–3.2 (2H), 3.85–4.33 (4H), 6.14 (1H) |
| 8 | $CH_3$ | H | $OC_4H_9$ | $C_4H_9$ | S | ($CDCl_3$, 60 MHz); 0.8–1.2 (6H), 1.25–1.95 (8H), 2.3 (3H), 3.9–4.37 (6H), 6.14 (1H). |
| 9 | $CH_3$ | H | $OC_3H_7$ | $C_3H_7$ | S | ($CDCl_3$, 60 MHz); 0.9 (6H), 1.68 (4H), 2.21 (3H), 3.7–4.28 (6H), 6.06 (1H). |
| 10 | $CH_3$ | $CH_3$ | $OC_2H_5$ | $C_2H_5$ | S | ($CDCl_3$, 60 MHz), 1.25 (3H), 1.74 (3H), 2.24 (3H), 3.75–4.77 (2H), 5.05 (1H), 6.05 (1H) |
| 11 | $C_2H_5$ | H | $S$-$n$-$C_3H_7$ | $C_2H_5$ | O | ($CDCl_3$, 60 MHz); 0.98 (3H), 1.23 (3H), 1.33 (3H), 1.68 (2H) 2.4–3.15 (4H), 3.85–4.32 (4H), 6.17 (1H). |
| 12 | $CH_3$ | H | $S$-$n$-$C_4H_9$ | $C_2H_5$ | O | ($CDCl_3$, 60 MHz); 0.94 (3H), 1.2–1.8 (4H), 2.23 (3H), 2.83 (2H) 3.9–4.35 (4H), 6.12 (1H.) |

-continued

| No. | R¹ | R² | R³ | R⁴ | X | MHz nmr spectrum δ-values (LM) |
|---|---|---|---|---|---|---|
| 13 | CH₃ | H | SCH₃ | C₂H₅ | O | (CDCl₃, 60 MHz); 1.32 (3H), 2.24 (3H), 2.46 (3H), 3.9–4.4 (4H), 6.12 (1H). |
| 14 | CH₃ | H | OCH₃ | CH₃ | O | (CDCl₃, 220 MHz); 2.15 (3H), 3.48 (6H), 3.74 (2H), 5.6 (1H). |
| 15 | CH₃ | H | NH—CH(CH₃)₂ | CH₃ | O | (CDCl₃, 60 MHz); 1.2 (6H), 2.3 (3H), 3.0 (1H), 3.75 (3H), 4.07 (2H), 6.2 (1H). |
| 16 | CH₃ | H | —N(CH₃)₂ | CH₃ | O | (CDCl₃, 60 MHz); 2.13 (3H), 2.54 (6H), 3.61 (3H), 3.94 (2H), 6.02 (1H). |
| 17 | CH₃ | H | S—CH₂—C≡C—CH₃ | C₂H₅ | O | (CDCl₃, 60 MHz); 1.34 (3H), 1.76 (3H), 2.22 (3H), 3.53 (2H), 3.9–4.4 (4H), 6.07 (1H). |
| 18 | CH₃ | H | SCH₃ | CH₃ | O | (CDCl₃, 100 MHz); 2.26 (3H), 2.36 (3H), 3.81 (3H), 4.16 (2H), 2.22 (1H). |
| 19 | CH₃ | H | OCH₃ | CH₃ | S | (CDCl₃, 60 MHz); 2.14 (3H), 3.7 (3H), 4.15 (2H), 6.23 (1H). |
| 20 | n-C₃H₇ | C₂H₅ | S-n-C₃H₇ | C₂H₅ | O | |
| 21 | i-C₃H₇ | H | S-i-C₃H₇ | C₂H₅ | O | |
| 22 | i-C₃H₇ | CH₃ | SC₂H₅ | CH₃ | S | |
| 23 | i-C₄H₉ | H | OC₂H₅ | C₂H₅ | S | |
| 24 | i-C₃H₇ | H | NH—CH(CH₃)₂ | CH₃ | O | |
| 25 | i-C₃H₇ | C₃H₇-i | S-i-C₃H₇ | C₂H₅ | O | |
| 26 | i-C₃H₇ | H | —N(CH₃)₂ | C₂H₅ | O | |
| 27 | C₂H₅ | C₂H₅ | S-n-C₃H₇ | C₂H₅ | O | |
| 28 | i-C₃H₇ | H | S—CH(CH₃)₂ | CH₃ | O | |
| 29 | i-C₃H₇ | H | S—CH(C₂H₅)₂ | C₂H₅ | O | (CDCl₃, 60 MHz); 0.95 (3H); 1.1–1.5 (6H+6H); 1.59 (2H); 2.5–3.5 (1H+1H); 4.0 (2H); 6.03 (1H). |
| 30 | n-C₅H₁₁ | CH₃ | S-n-C₃H₇ | C₂H₅ | O | |
| 31 | (C₂H₅)₂CH— | H | S-n-C₃H₇ | C₂H₅ | O | |
| 32 | C₃H₇(CH₃)CH— | H | S-n-C₃H₇ | C₂H₅ | O | |
| 33 | C₃H₇(C₂H₅)CH— | CH₃ | S-n-C₃H₇ | C₂H₅ | O | |
| 34 | CH₃(C₂H₅)CH— | H | S-i-C₃H₇ | C₂H₅ | O | |
| 35 | C₂H₅ | H | —NH—CH(CH₃)₂ | CH₃ | O | (CDCl₃, 60MHz); 1.2(6H); 1.25(3H); 1.92(1H); 2.67(2H); 3.68(3H); 4.02(2H); 6.11(1H) |
| 36 | C₂H₅ | H | —OCH₃ | CH₃ | O | (CDCl₃, 60 MHz); 1.22(3H); 2.63(2H); 3.71(6H); 4.06(2H); 6.14(1H) |
| 37 | i-C₃H₇ | H | OCH₃ | CH₃ | O | |
| 38 | i-C₃H₇ | H | S-n-C₃H₇ | C₂H₅ | O | (CDCl₃, 60 MHz); 0.98(3H); 1.03–2.0 (6H+3H+2H); 2.4–3.5(2H+1H); 3.95–4.4 (2H); 4.13(2H); 6.13(1H) |

-continued

| No. | R¹ | R² | R³ | R⁴ | X | MHz nmr spectrum δ-values (LM) |
|---|---|---|---|---|---|---|
| 39 | i-C₃H₇ | i-C₃H₇ | S-n-C₃H₇ | C₂H₅ | O | |
| 40 | C₂H₅ | C₂H₅ | S-i-C₃H₇ | C₂H₅ | O | |
| 41 | CH₃ | H | SC₂H₅ | n-C₃H₇ | O | (CDCl₃, 60 MHz); 0.85 (3H); 1.26 (3H); 2.51 (2H); 2.12 (3H); 2.8 (2H); 3.9 (2H); 3.95 (2H); 6.01 (1H) |
| 42 | C₂H₅ | H | SC₂H₅ | n-C₃H₇ | O | (CDCl₃, 60 MHz); 0.93 (3H); 1.25 (3H); 1.39 (3H); 1.66 (2H); 2.4–3.15 (2H+2H); 3.8–4.3 (2H); 4.08 (2H); 6.12 (1H) |
| 43 | i-C₃H₇ | H | OC₂H₅ | C₂H₅ | S | (CDCl₃, 60 MHz); 1.13–1.5 (6H+6H); 2.89 (1H); 3.7–4.35 (4H); 4.03 (2H); 6.07 (1H) |
| 44 | i-C₃H₇ | H | SC₂H₅ | n-C₃H₇ | O | (CDCl₃, 60 MHz); 0.88 (3H); 1.2 (6H); 1.25 (3H); 1.53 (2H); 2.4–3.2 (2H+1H); 3.75–4.1 (2H); 4.0 (2H); 6.02 (1H) |
| 45 | CH₃ | H | S-CH(CH₃)C₂H₅ | C₂H₅ | O | (CDCl₃, 60 MHz); 0.96 (3H); 1.28 (3H); 1.40 (3H); 1.64 (2H); 2.25 (3H); 3.3 (1H); 4.12 (2H); 4.2 (2H); 6.16 (1H) |
| 46 | C₂H₅ | H | S-CH(CH₃)C₂H₅ | C₂H₅ | O | (CDCl₃, 60 MHz); 0.98 (3H); 1.21 (3H); 1.36 (3H+3H); 1.66 (2H); 2.68 (2H); 3.37 (1H); 4.19 (2H); 4.32 (2H); 6.19 (1H) |
| 47 | CH₃ | H | S-i-C₃H₇ | CH₃ | O | (CDCl₃, 60 MHz); 1.41 (6H); 2.25 (3H); 3.15–3.9 (1H); 3.8 (3H); 4.1 (2H); 6.1 (1H); |
| 48 | CH₃ | H | S-n-C₃H₇ | CH₃ | O | (CDCl₃, 60 MHz); 0.95 (3H); 1.7 (2H); 2.2 (3H); 2.8 (2H); 4.72 (3H); 4.37 (2H); 6.02 (1H) |
| 49 | CH₃ | H | S-t-C₄H₉ | C₂H₅ | O | (CDCl₃, 80 MHz); 1.31 (3H); 1.59 (9H); 2.26 (3H); 3.9–4.3 (2+2H); 6.1 (1H); |
| 50 | CH₃ | H | S-i-C₄H₉ | C₂H₅ | O | (CDCl₃, 60 MHz); 0.98 (6H); 1.3 (3H); 1.52–2.33 (1H); 2.18 (3H); 2.5–2.9 (2H); 3.8–4.3 (4H); 6.05 (1H); |
| 51 | C₂H₅ | H | S-i-C₄H₉ | C₂H₅ | O | (CDCl₃, 100 MHz) 1.02 (6H); 1.21 (3H); 1.34 (3H); 1.92 (1H); 2.68 (2H); 2.81 (2H); 4.12 (2H); 4.15 (2H); 6.14 (1H) |
| 52 | i-C₃H₇ | H | S-i-C₄H₉ | C₂H₅ | O | (CDCl₃, 100 MHz) 1.02 (6H); 1.2 (6H); 1.33 (3H); 1.93 (1H); 2.78 (1H); 2.96 (1H); 4.0–4.3 (2H+2H); 6.14 (1H) |
| 53 | i-C₄H₉ | H | S-i-C₄H₉ | C₂H₅ | O | (CDCl₃, 60 MHz) 0.8–1.2 (6H+6H); 1.37 (3H); 1.95 (2H); 2.5 (2H); 2.88 (2H); 3.9–4.4 (2H+2H); 6.11 (1H) |
| 54 | t-C₄H₉ | H | S-i-C₄H₉ | C₂H₅ | O | (CDCl₃, 60 MHz) 0.098 (6H); 1.27 (9H); 1.31 (3H); 1.9 (1H); 2.71 (2H); 4.05 (2H); 4.13 (2H); 6.12 (1H) |
| 55 | n-C₃H₇ | H | S-i-C₃H₇ | C₂H₅ | O | (CDCl₃, 60 MHz) 0.97 (3H); 1.33 (3H); 1.43 (6H); 1.6 (2H); 1.63 (2H); 3.56 (1H); 4.18 (2H); 4.26 (2H); 6.14 (1H) |

-continued

| No. | R$^1$ | R$^2$ | R$^3$ | R$^4$ | X | MHz nmr spectrum δ-values (LM) |
|---|---|---|---|---|---|---|
| 56 | i-C$_4$H$_9$ | H | S-i-C$_3$H$_7$ | C$_2$H$_5$ | O | (CDCl$_3$, 60 MHz) 0.9 (6H); 1.22 (3H); 1.21 (6H); 1.84 (1H); 2.47 (2H); 3.4 (1H); 3.9–4.2 (2H+2H); 6.01 (1H) |
| 57 | n-C$_4$H$_9$ | H | S-n-C$_3$H$_7$ | C$_2$H$_5$ | O | (CDCl$_3$, 60 MHz) 0.77 (3H); 0.84 (3H); 1.0–1.83 (3H+4H+2H); 2.45 (2H); 2.87 (2H); 4.0 (2H); 4.09 (2H); 6.01 (1H) |
| 58 | n-C$_3$H$_7$ | H | S-n-C$_3$H$_7$ | C$_2$H$_5$ | O | (CDCl$_3$, 60 MHz) 1.04 (6H); 1.43 (3H); 1.5–2.1 (4H); 2.7 (2H); 3.01 (2H); 4.21 (2H); 4.3 (2H); 6.18 (1H) |
| 59 | sec-C$_4$H$_9$ | H | S-n-C$_3$H$_7$ | C$_2$H$_5$ | O | (CDCl$_3$, 60 MHz) 0.8 (3H); 0.91 (3H); 1.0–1.9 (3H+3H+4H); 2.5–3.05 (1H+2H); 4.03 (2H); 4.16 (2H); 6.04 (1H) |
| 60 | t-C$_4$H$_9$ | H | S-n-C$_3$H$_7$ | C$_2$H$_5$ | O | (CDCl$_3$, 60 MHz) 1.05 (3H); 1.36 (9H); 1.40 (3H); 1.75 (2H); 2.9 (2H); 4.22 (2H); 4.3 (2H); 6.3 (1H) |

Application of the active ingredients may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methyl-pyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products or sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol, polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tankmix)) oils of various types, herbicides, fungicides, nematocides, insecticides, and bactericides.

These agents may be added to the agents according to the invention in a ratio by weight of from 1:10 to 10:1.

The active ingredients according to the invention may be used for combatting pests such as sucking and biting insects, Diptera and mites.

The main representatives of the sucking insects are aphids (Aphidae) such as *Myzus persicae, Doralis fabae, Rhopalosiphum padi., Macrosiphum pisi, Macrosiphum solanifolii, Cryptomyzus korschelti, Sapaphis mali, Hyalopterus arundinis* and *Myzus cerasi,* and bugs such as *Piesma quadratum, Dysdercus intermedius, Cimex lectularius, Rhodnius prolixus* and *Triatoma infestans.*

The most important of the biting insects are Lepidoptera such as *Prodenia litura, Plutella maculipennis, Lymantria dispar., Euproctis chrysorrhoea* and *malacosoma neustria,* further *Mamestra brassicae, Agrotis segetum, Pieris brassicae, Hyponomeuta padella, Ephestia kuhniella* and *Galleria mellonella.*

Other representatives of biting insects are beetles (Coleoptera) such as *Sitophilus granarius, Leptinotarsa decemlineata, Dermestes frischi, Tribolium castaneum, Calandra* or *Sitophilus zeamais, Stegobium paniceum, Tenebrio molitor,* including soil-borne species such as wireworms (*Agriotes* spec.) and cockchafers (*Melolontha melolontha*); cockroaches such as *Blatella germanica, Periplaneta americana, Blatta orientalis, Blaberus giganteus, Blaberus fuscus,* and *Henschoutedenia flexivitta;* Orthoptera, e.g., *Acheta domestica,* termites such as *Reticulitermes flavipes,* and Hymenoptera such as ants, e.g., *Lasius niger.*

The Diptera essentially encompass flies such as *Drosophila melanogaster, Ceratitis capitata, Musca domestica, Fannia canicularis, Phormia regina, Calliphora erythrocephala* and *Stomoxys calcitrans;* mosquitoes such as *Aedes aegypti, Culex pipiens* and *Anopheles stephensi.*

Of the mites (Acari) particular importance attaches to spider mites (Tetranychidae) such as *Tetranychus telarius* (=*Tetranychus althaeae* or *Tetranychus urticae*) and *Paratetranychus pilosus* (=*Panonychus ulmi*); gall mites, e.g., *Eriophyes ribis,* and Tarsonemidae, e.g., *Hemitarsonemus latus* and *Tarsonemus pallidus;* and finally ticks such as *Ornithodorus moubata.*

The following examples demonstrate the biological action.

For comparison purposes the following prior art compounds are used:

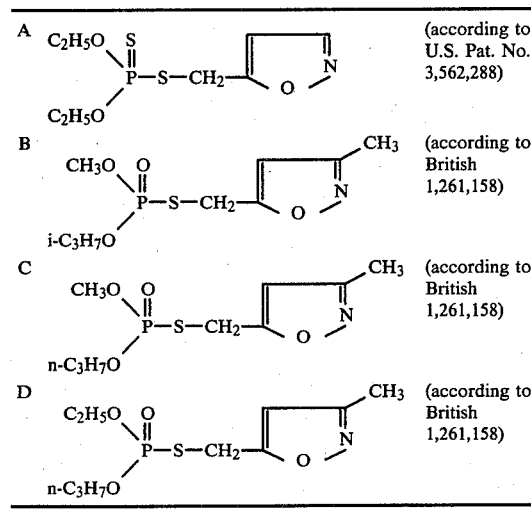

A  (according to U.S. Pat. No. 3,562,288)
B  (according to British 1,261,158)
C  (according to British 1,261,158)
D  (according to British 1,261,158)

EXAMPLE 1

Contact action on bean aphids (*Aphis fabae*)

Potted bean plants (*Vicia faba*) severely afflicted with aphid colonies are sprayed to runoff in a spray cabinet with aqueous active ingredient formulations.

Assessment takes place after 24 hours.

Results: Mortality (in %)

| Concentration of active ingredient formulation | | 0.04% | 0.02% | 0.01% | 0.005% | 0.0025% |
|---|---|---|---|---|---|---|
| Compound no. | 19 | 100 | 100 | 100 | 100 | 100 |
| | 2 | 100 | 100 | 100 | 80 | |
| | 17 | 80 | | | | |
| | 14 | 100 | 100 | 100 | 100 | |
| | 1 | 100 | 100 | 100 | 80 | |
| | 15 | 100 | 100 | 100 | 100 | |
| | 16 | 100 | 80 | | | |
| | 13 | 100 | 100 | 100 | | |
| | 12 | 100 | 100 | | | |
| | 7 | 100 | 100 | | | |
| | 5 | 100 | 100 | 100 | | |
| | 4 | 100 | 100 | 100 | 80 | |
| | 10 | 100 | 100 | 80 | | |

EXAMPLE 2

Contact action on cockroaches (*Blatta orientalis*)

Acetonic active ingredient solutions of various concentrations are applied to the bottom of preserving jars.

After the solvent has evaporated, 5 adult cockroaches are placed in each jar. The mortality is determined after 48 hours.

Results: Mortality (in %)

| Amount of active ingredient per preserving jar | | 0.5 mg | 0.25 mg | 0.1 mg |
|---|---|---|---|---|
| Compound no. | 19 | 100 | 20 | |
| | 2 | 100 | 100 | 100 |
| | 17 | 100 | 100 | 40 |
| | 15 | 100 | 20 | |
| | 12 | 100 | 100 | 40 |
| | 7 | 100 | 100 | 20 |
| | 5 | 100 | 100 | 60 |
| | 10 | 100 | 100 | 40 |

EXAMPLE 3

Continuous contact action on houseflies (*Musca domestica*)

Both covers and bottoms of Petri dishes 10 cm in diameter are lined with a total of 2 ml of acetonic active ingredient solutions of various concentrations. After the solvent has evaporated (about 30 minutes), 10 flies are introduced into each dish. The mortality is determined after 4 hours.

Results: Mortality (in %)

| Amount of active ingredient per dish | | 0.2 mg | 0.02 mg | 0.01 mg | 0.005 mg |
|---|---|---|---|---|---|
| Compound no. | 19 | 100 | 100 | 30 | |
| | 2 | 100 | 100 | 100 | 80 |
| | 18 | 80 | | | |
| | 14 | 100 | 40 | | |
| | 1 | 100 | 80 | | |
| | 15 | 100 | 20 | | |
| | 5 | 80 | | | |

-continued

Results: Mortality (in %)

| Amount of active ingredient per dish | 0.2 mg | 0.02 mg | 0.01 mg | 0.005 mg |
|---|---|---|---|---|
| | 10 | 100 | 100 | 20 |

EXAMPLE 4

Contact action on cotton stainers (*Dysdercus intermedius*)

Petri dishes 10 cm in diameter are lined with 1 ml of aceto active ingredient solutions of various concentrations.

After the solvent has evaporated, 20 larvae of the penultimate stage are placed in each dish and the action is registered after 24 hours.

Results: Mortality (in %)

| Amount of active ingredient per dish | | 0.1 mg | 0.02 mg | 0.01 mg | 0.005 mg | 0.0025 mg |
|---|---|---|---|---|---|---|
| Compound no. | 19 | 100 | 100 | 100 | 80 | |
| | 2 | 100 | 80 | | | |
| | 17 | 100 | 20 | | | |
| | 14 | 100 | 100 | 100 | 100 | 100 |
| | 1 | 100 | 40 | | | |
| | 16 | 100 | 70 | | | |
| | 5 | 100 | 80 | | | |
| | 10 | 100 | 40 | | | |

EXAMPLE 5

Contact action on ticks (*Ornithodorus moubata*)

Ticks in the third larval stage are placed in tea-bags which are then dipped for 3 seconds in emulsions of various concentrations. The bags are then suspended. After 48 hours the action on the ticks is assessed.

Results: Mortality (in %)

| Concentration of the emulsion | | 0.04% | 0.02% | 0.01% | 0.005% |
|---|---|---|---|---|---|
| Compound no. | 19 | 100 | 100 | 100 | 100 |
| | 2 | 100 | 100 | 100 | |
| | 18 | 100 | | | |
| | 17 | 100 | 100 | 100 | |
| | 1 | 100 | 100 | 80 | |
| | 5 | 100 | | | |
| | 4 | 100 | 100 | 100 | |

EXAMPLE 6

Contact action and effect of ingested food on caterpillars of the diamond back moth (*Plutella maculipennis*)

Leaves of young cabbage plants are dipped for 3 seconds in aqueous emulsions of the active ingredients. After briefly allowing excess emulsion to drip off, the leaves are placed on a moist filter paper in a Petri dish. 10 caterpillars in the fourth larval stage are then placed on each leaf.

The action is assessed after 48 hours.

Results: Mortality (in %)

| Concentration of active ingredient emulsion | | 0.05% | 0.02% | 0.01% | 0.005% |
|---|---|---|---|---|---|
| Compound no. | 19 | 100 | 80 | | |
| | 2 | 100 | 100 | 100 | 80 |
| | 14 | 100 | 70 | | |
| | 15 | 100 | 80 | | |
| | 12 | 100 | 100 | 80 | |
| | 7 | 100 | 70 | | |
| | 5 | 100 | 100 | 80 | |
| | A | 100 | 40 | | |

EXAMPLE 7

Action on caterpillars of the beet armyworm (*Laphygma exigua*)

Freshly cut leaves of Indian corn are dipped for 3 seconds in aqueous formulations of the active ingredients. After briefly allowing excess liquid to drip off, the leaves are placed on a circular filter paper in Petri dishes having a diameter of 10 cm 5 caterpillars about 1.5 cm in length are then placed on each leaf.

The action is assessed after 48 hours.

Results: Mortality (in %)

| Concentration of active ingredient emulsion | | 0.05% | 0.025% | 0.0125% | 0.0025% |
|---|---|---|---|---|---|
| Compound no. | 2 | 100 | 100 | 100 | 100 |
| | 7 | 100 | 100 | 20 | |
| | 5 | 100 | 100 | 100 | |
| | 11 | 100 | 100 | 100 | |
| A | | 80 | | | |

EXAMPLE 8

Action on *Prodenia litura*

Freshly out leaves of Indian corn were dipped for 3 seconds in aqueous formulations of the active ingredients. After briefly having allowed excess liquid to drip off, the leaves were placed on a circular filter paper (9 cm in diameter) in Petri dishes. 5 caterpillars in the third larval stage and about 1.5 cm in length were then placed on each leaf. The action was assessed after 48 hours.

Results: Mortality (in %)

| Concentration of active ingredient emulsion | | 0.1% | 0.05% | 0.04% | 0.02% | 0.01% |
|---|---|---|---|---|---|---|
| Compound no. | 2 | | | | 100 | 70 |
| | D | ineffective | | | | |
| | 47 | 60 | | | | |
| | B | ineffective | | | | |
| | 48 | | 100 | | | 60 |
| | 6 | ineffective | | | | |
| | 50 | | | 90 | | |

EXAMPLE 9

Contact action on houseflies (*Musca domestica*); administration test

1 μl of the active ingredient dissolved in acetone was administered by means of a microsyringe to the ventral abdomen of 4-day old imagoes under slight $CO_2$ narcosis. 20 animals having been subjected to identical treatment were then placed in a cellophane bag.

The mortality was determined after 4 hours and the $LD_{50}$ calculated from the concentrations.

| Compound no. | $LD_{50}$ (μg/fly) |
|---|---|
| 2 | 0.14 |
| D | 0.65 |
| 47 | 0.3 |
| B | 0.6 |
| 48 | 0.26 |
| C | 0.65 |

EXAMPLE 10

Contact action on cockroaches (*Blatta orientalis*)

Acetonic solutions in varying concentrations are prepared from active ingredients nos. 2, 12, 47 and 48 according to the invention and comparison compounds B, C and D. A certain volume of these solutions is applied to the bottom of preserving jars; after the solvent has evaporated, the jar bottom is lined with the active ingredient.

5 adult cockroaches are then placed on the treated bottom of each of the preserving jars. The mortality rate in % achieved with certain amounts of active ingredient (given in mg) is determined after 48 hours.

| Mortality (in %) | 100 | 90 | 60 | <60 |
|---|---|---|---|---|
| Compound no. 2 | | | 0.02 mg | |
| D | | | 0.2 mg | |
| 47 | 0.5 mg | | | 0.2 mg |
| B | 0.5 mg | | | 0.2 mg |
| 48 | 0.5 mg | | | 0.2 mg |
| C | | 0.1 mg | | |
| 12 | 0.5 mg | | | 0.1 mg |

EXAMPLE 11

Contact action and effect of ingested food on caterpillars of the diamondback moth (*Plutella maculipennis*)

Caterpillars in the fourth larval stage are selected for each experiment. 10 of these animals are placed in each case on a leaf from a young cabbage plant, the leaf having previously been treated by dipping it for 3 seconds in aqueous emulsions of the compounds given in the table; after excess emulsion has been allowed to run off, the leaf is placed on a moist filter paper 9 cm in diameter in a Petri dish. The percentage mortality rate achieved after 48 hours with the compounds at certain active ingredient concentrations of the aqueous emulsions (in %) is given in the table below.

| Mortality (in %) | 100 | 80 | 70 |
|---|---|---|---|
| Compound no. 2 | | 0.01% | |
| D | | 0.04% | |
| 47 | | 0.04% | |
| B | | 0.04% | |
| 48 | 0.02% | | |
| C | | 0.02% | |
| 12 | 0.05% | 0.01% | |
| 50 | | | 0.05% |

EXAMPLE 12

Action on caterpillars of the beet armyworm (*Laphygma exigua*)

Circular filter papers 10 cm in diameter are placed in Petri dishes. On the filter papers are placed leaves of Indian corn which have been dipped for 3 seconds in aqueous emulsions of the active ingredients immediately after having been cut from the plant. 5 caterpillars in the third larval stage (approx. 1.5 cm in length) are then placed on each of the leaves.

Mortality counts are made after 48 hours. Results: Active ingredient concentration in the aqueous emulsion at which a certain mortality rate is achieved.

| Mortality (in %) | 100 | 90 | 80 | 60 | <60 |
|---|---|---|---|---|---|
| Compound no. 2 | | | 0.005% | | |
| D | | | | | 0.01% |
| 47 | 0.025% | | | 0.02% | |
| B | | 0.1% | | | 0.05% |
| 48 | 0.05% | | | | 0.01% |
| C | 0.05% | | | 0.01% | |
| 12 | 0.025% | 0.0125% | | | |
| 50 | 0.02% | | 0.01% | 0.005% | |

EXAMPLE 13

Continuous contact action on houseflies (*Musca domestica*)

10 flies are used for each of the experiments.

2 ml of acetonic active ingredient solutions in varying concentrations is introduced into the cover and 2 ml into the bottom of Petri dishes 10 cm in diameter. The solvent has evaporated after about 30 minutes; the dishes are then lined with a fine layer of active ingredient. 10 flies are placed in each dish. The mortality rate in % is ascertained after 48 hours.

| Amount of active ingredient per dish | Results: Mortality (in %) | |
|---|---|---|
| | 0.2 mg | 0.02 mg |
| Compound no. 2 | 100 | 80 |
| D | 100 | ineffective |
| 47 | 100 | ineffective |
| B | 100 | ineffective |
| 48 | 100 | 80 |
| C | 100 | 80 |
| 12 | 100 | ineffective |

We claim:
1. Phosphoric acid derivative of the formula

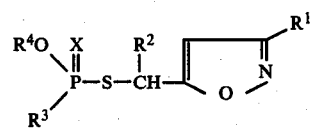

where X denotes oxygen or sulfur, $R^1$ denotes identical or different, linear or branched alkyl groups of a maximum of 6 carbon atoms, $R^2$ denotes hydrogen or alkyl of a maximum of 3 carbon atoms, $R^3$ denotes propylthio or butylthio and $R^4$ denotes ethyl.

2.

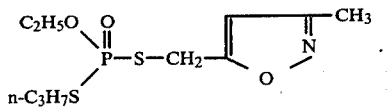

3.

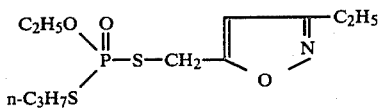

4.

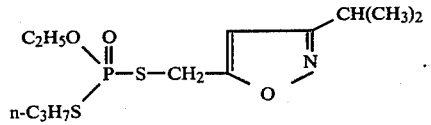

5.

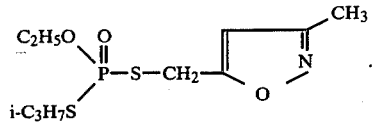

6.

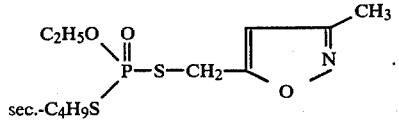

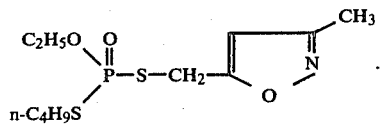

8. A pesticide consisting essentially of a solid or liquid carrier and an effective amount of a phosphoric acid derivative of the formula I

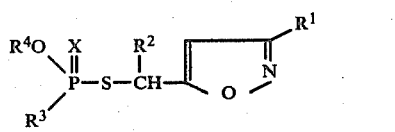

where X denotes oxygen or sulfur, $R^1$ denotes identical or different, linear or branched alkyl groups of a maximum of 6 carbon atoms, $R^2$ denotes hydrogen or alkyl of a maximum of 3 carbon atoms, $R^3$ denotes propylthio or butylthio and $R^4$ denotes ethyl, as active ingredient.

9. A process for controlling pests, wherein the pests or the objects to be protected against pest attack are treated with an effective amount of a phosphoric acid derivative of the formula I

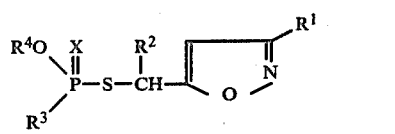

where X denotes oxygen or sulfur, $R^1$ denotes identical or different, linear or branched alkyl groups of a maximum of 6 carbon atoms, $R^2$ denotes hydrogen or alkyl of a maximum of 3 carbon atoms, $R^3$ denotes propylthio or butylthio and $R^4$ denotes ethyl.

10. A process as set forth in claim 9, wherein the pests are sucking and biting insects.

11. A process as set forth in claim 9, wherein the pests are Lepidoptera.

12. A phosphoric acid derivative as set forth in claim 1 wherein $R^3$ is isobutylthio.

* * * * *